(12) United States Patent
Cheng et al.

(10) Patent No.: US 7,956,033 B2
(45) Date of Patent: Jun. 7, 2011

(54) MODIFIED PEPTIDE OF HUMAN ACIDIC FIBROBLAST GROWTH FACTOR

(75) Inventors: Henrich Cheng, Taipei (TW); Wen-Chun Kuo, Taipei (TW)

(73) Assignee: Eu Sol Biotech Co., Ltd., Taipei (TW)

( * ) Notice: Subject to any disclaimer, the term of this patent is extended or adjusted under 35 U.S.C. 154(b) by 0 days.

(21) Appl. No.: 12/482,041

(22) Filed: Jun. 10, 2009

(65) Prior Publication Data

US 2009/0305988 A1    Dec. 10, 2009

Related U.S. Application Data

(60) Provisional application No. 61/060,262, filed on Jun. 10, 2008.

(51) Int. Cl.
*A61K 38/18*    (2006.01)
*C07K 14/50*    (2006.01)

(52) U.S. Cl. .......................... 514/9.1; 530/350; 530/399

(58) Field of Classification Search ........................ None
See application file for complete search history.

(56) References Cited

U.S. PATENT DOCUMENTS

| 7,282,481 B2 * | 10/2007 | Imamura et al. .................. 514/8 |
| 7,741,078 B2 * | 6/2010 | Imamura et al. ............. 435/69.7 |
| 2009/0305988 A1 | 12/2009 | Cheng et al. |

FOREIGN PATENT DOCUMENTS

| DE | 11 2005 000 737 | | 4/2007 |
| JP | 2000236880 | * | 9/2000 |
| WO | 02/14471 A2 | | 2/2002 |
| WO | WO 2005/095600 | * | 10/2005 |

* cited by examiner

*Primary Examiner* — Marianne P Allen
(74) *Attorney, Agent, or Firm* — Occhiuti Rohlicek & Tsao LLP (57) ABSTRACT

An modified peptide of human acidic fibroblast growth factor (aFGF), comprising a native human aFGF shortened by a deletion of a deletion of 20 amino acids from N-terminal of the native human aFGF, and an addition of Alanine (Ala) before the shortened native aFGF is provided.

2 Claims, 7 Drawing Sheets

SEQUENCE LISTING

<160> NUMBER OF SEQ ID NOS: 7

<210> SEQ ID NO 1
<211> LENGTH: 135
<212> TYPE: PRT
<213> ORGANISM: Artificial
<220> FEATURE:
<223> OTHER INFORMATION: Peptide derived from Homo sapiens
      Acid-Fibroblast Growth Factor (a-FGF)

<400> SEQUENCE: 1

```
Ala Asn Tyr Lys Lys Pro Lys Leu Leu Tyr Cys Ser Asn Gly Gly His
1               5                   10                  15

Phe Leu Arg Ile Leu Pro Asp Gly Thr Val Asp Gly Thr Arg Asp Arg
            20                  25                  30

Ser Asp Gln His Ile Gln Leu Gln Leu Ser Ala Glu Ser Val Gly Glu
        35                  40                  45

Val Tyr Ile Lys Ser Thr Glu Thr Gly Gln Tyr Leu Ala Met Asp Thr
    50                  55                  60

Asp Gly Leu Leu Tyr Gly Ser Gln Thr Pro Asn Glu Glu Cys Leu Phe
65                  70                  75                  80

Leu Glu Arg Leu Glu Glu Asn His Tyr Asn Thr Tyr Ile Ser Lys Lys
                85                  90                  95

His Ala Glu Lys Asn Trp Phe Val Gly Leu Lys Lys Asn Gly Ser Cys
            100                 105                 110

Lys Arg Gly Pro Arg Thr His Tyr Gly Gln Lys Ala Ile Leu Phe Leu
        115                 120                 125

Pro Leu Pro Val Ser Ser Asp
    130                 135
```

<210> SEQ ID NO 2
<211> LENGTH: 28
<212> TYPE: DNA
<213> ORGANISM: Artificial
<220> FEATURE:
<223> OTHER INFORMATION: primer

<400> SEQUENCE: 2
actgaattca tggctgaagg ggaaatca                                       28

<210> SEQ ID NO 3
<211> LENGTH: 30
<212> TYPE: DNA
<213> ORGANISM: Artificial
<220> FEATURE:
<223> OTHER INFORMATION: primer

<400> SEQUENCE: 3
aagaagcttc aatcagaaga gactggcagg                                     30

<210> SEQ ID NO 4
<211> LENGTH: 26
<212> TYPE: DNA
<213> ORGANISM: Artificial
<220> FEATURE:
<223> OTHER INFORMATION: primer

<400> SEQUENCE: 4
ggcatatggc taattacaag aagccc                                         26

<210> SEQ ID NO 5

```
<211> LENGTH: 33
<212> TYPE: DNA
<213> ORGANISM: Artificial
<220> FEATURE:
<223> OTHER INFORMATION: primer

<400> SEQUENCE: 5
aagagatctc tttaatcaga agagactggc agg                                     33

<210> SEQ ID NO 6
<211> LENGTH: 140
<212> TYPE: PRT
<213> ORGANISM: Artificial
<220> FEATURE:
<223> OTHER INFORMATION: Peptide derived from Homo sapiens
      Acid-Fibroblast Growth Factor (a-FGF)

<400> SEQUENCE: 6

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 7
<211> LENGTH: 127
<212> TYPE: PRT
<213> ORGANISM: Artificial
<220> FEATURE:
<223> OTHER INFORMATION: Peptide derived from Homo sapiens
      Acid-Fibroblast Growth Factor (a-FGF)

<400> SEQUENCE: 7

Leu Tyr Cys Ser Asn Gly Gly His Phe Leu Arg Ile Leu Pro Asp Gly
1               5                   10                  15

Thr Val Asp Gly Thr Arg Asp Arg Ser Asp Gln His Ile Gln Leu Gln
            20                  25                  30

Leu Ser Ala Glu Ser Val Gly Glu Val Tyr Ile Lys Ser Thr Glu Thr
        35                  40                  45

Gly Gln Tyr Leu Ala Met Asp Thr Asp Gly Leu Leu Tyr Gly Ser Gln
    50                  55                  60

Thr Pro Asn Glu Glu Cys Leu Phe Leu Glu Arg Leu Glu Glu Asn His
65                  70                  75                  80

Tyr Asn Thr Tyr Ile Ser Lys Lys His Ala Glu Lys Asn Trp Phe Val
                85                  90                  95

Gly Leu Lys Lys Asn Gly Ser Cys Lys Arg Gly Pro Arg Thr His Tyr
            100                 105                 110
```

```
                                     -continued
Gly Gln Lys Ala Ile Leu Phe Leu Pro Leu Pro Val Ser Ser Asp
        115                 120                 125
```

MODIFIED PEPTIDE OF HUMAN ACIDIC FIBROBLAST GROWTH FACTOR

CROSS-REFERENCE TO RELATED APPLICATION PARAGRAPH

This application claims the benefit of U.S. Provisional Application No. 60/060,262 filed on Jun. 10, 2008, the content of which is hereby incorporated by reference in its entirety.

FIELD OF THE INVENTION

The present invention is related to a modified peptide of acidic fibroblast growth factor with a better stability.

BACKGROUND OF THE INVENTION

Acidic fibroblast growth factor (aFGF), which influences the proliferation and differentiation of various cell types in vitro, were originally isolated as single chain proteins from neural tissue, including whole brain and hypothalamus. The aFGF is a heparin-dependent mitogen and it can strongly bind on all four known FGF receptors and their spliced form. It can be localized within specific subsets of neurons associated with motor and sensory functions, and can be purified from the adult brain. Purified aFGF is a mitogen for neuroblasts and promotes the neurites extension from spinal cord neurons.

Native peptide of human aFGF is isolated from human brain, and consists of 154 amino acids. However, 19 amino acids in N-terminal of the native human aFGF have been identified homogenous with human interleukin-1 (IL-1). The similar domain of polypeptide between human aFGF and IL-1 may cause the same endogenous immuno-response, including activation of macrophages, and modulated cells growth arrest (G. Venkataraman et al., *P.N.A.S.*, 96:3658-63, 1999). Furthermore, the pro-inflammatory cytokine IL-1 and FGF-1 (aFGF)/FGF-2 (bFGF) share the same structural scaffold and compete against the same receptor binding site of tyrosine kinase domains (A. J. Minter et al., *J. Cell Physil.*, 167:229-37, 1996).

BRIEF SUMMARY OF THE INVENTION

The invention provides an modified peptide of human acidic fibroblast growth factor (aFGF) named as aFGF135, comprising a native human aFGF shortened by a deletion of a deletion of 20 amino acids from N-terminal of the native human aFGF, and an addition of Alanine (Ala) before the shortened native aFGF. In particular, the peptide aFGF135 comprises the amino acid sequence of SEQ ID NO: 1, which has a relatively high stability and is better than known aFGF peptides.

The present invention further provides a pharmaceutical composition comprising the peptide aFGF135 of the invention and a pharmaceutically acceptable carrier.

BRIEF DESCRIPTION OF THE DRAWINGS

The foregoing summary, as well as the following detailed description of the invention, will be better understood when read in conjunction with the appended drawings. It should be understood, however, that the invention is not limited to the precise arrangements and instrumentalities shown.

In the drawings.

DETAILED DESCRIPTION OF THE INVENTION

This present invention provides an modified peptide of human acidic fibroblast growth factor (aFGF) named as aFGF135, comprising a native human aFGF shortened by a deletion of a deletion of 20 amino acids from N-terminal of the native human aFGF, and an addition of Alanine (Ala) before the shortened native aFGF. In particular, the peptide aFGF135 comprises the amino acid sequence of SEQ ID NO: 1. Unexpectedly, the modified peptide of the peptide aFGF135 has relatively high stability under physiology of temperature and has a distinct structure from other known aFGFs.

Figure 1A:
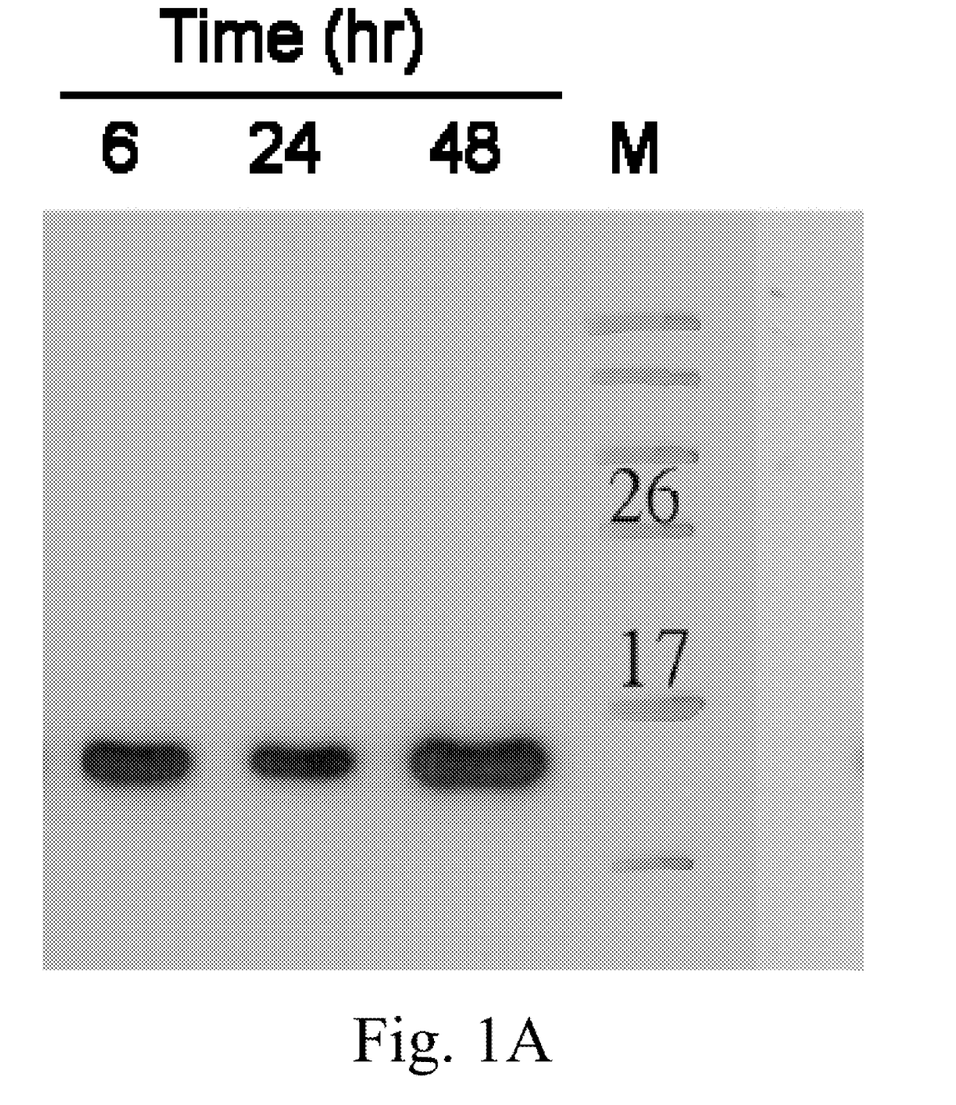
FIG. 1A is an image of the western blotting showing the degradation of the peptide aFGF135 after an incubation at 37° C. during a time period of 48 hours; wherein lanes 1 to 3 were the results after 6-hour, 24-hour and 48-hour incubation, respectively, and lane 4 was the molecular marker, and the number above each of the bands represented the molecular weight.
Figure 1B:
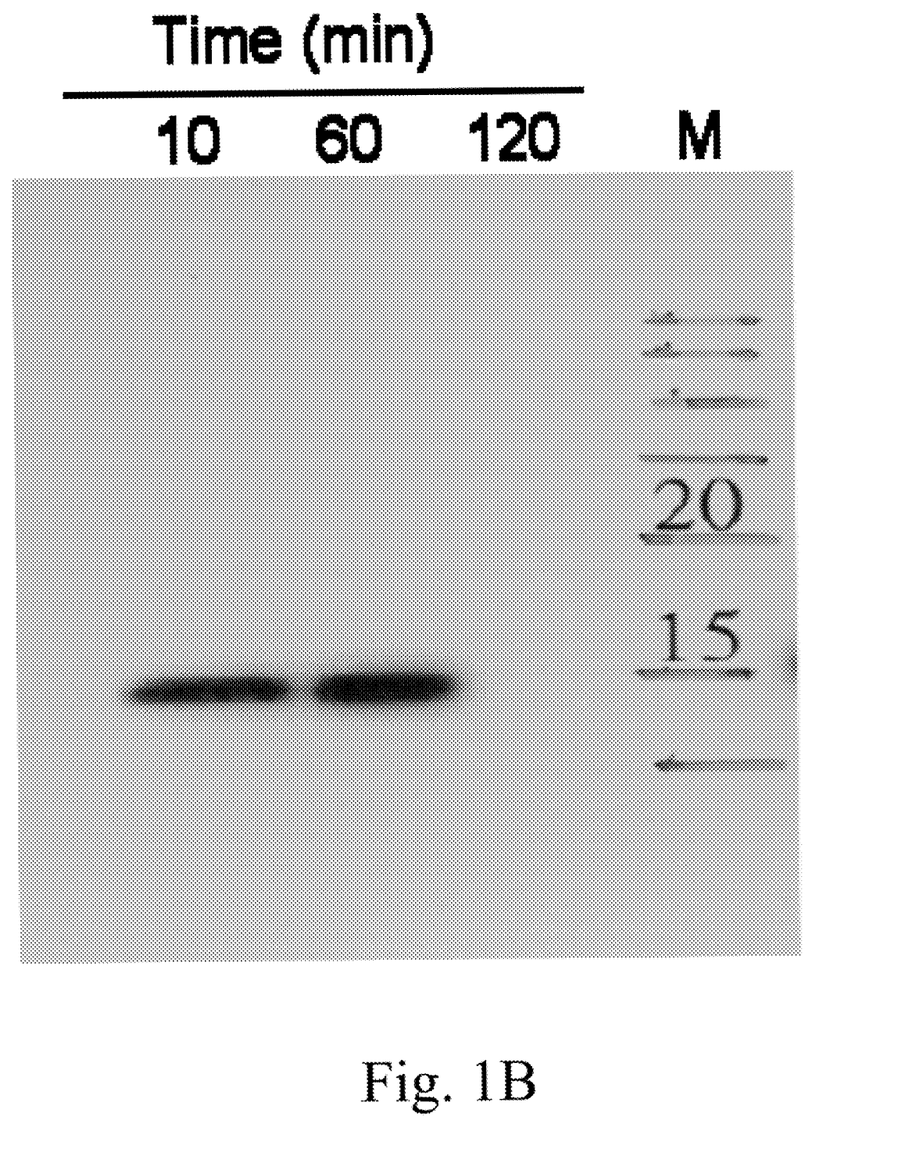
FIG. 1B is an image of the western blotting showing the degradation of the peptide aFGF135 after an incubation at 54° C. during a time period of 120 minutes (2 hours); wherein lanes 1 to 3 were the results after 10 minutes, 60 minutes and 120 minutes incubation, respectively, and lane 4 was the molecular marker, and the number above each of the bands represented the molecular weight.

According to the invention, the peptide aFGF135 has the amino acid sequence of SEQ ID NO: 1 with relatively high stability. As compared with the native human aFGFs, the peptide aFGF135 has a deletion of 20 amino acids from N-terminal of the native human aFGF (called as "the shortened aFGF") and an addition of Alanine (Ala) before the 20 a.a. deleted aFGF. According to the invention, the 20 amino acids were deleted from the native human aFGF to avoid the IL-1-like effects via the common pathway because the first 19 amino acids of human aFGF have been identified homogenous with human interleukin-1 (IL-1), and were deleted. It was unexpectedly discovered that the peptide aFGF has outstanding stability under physiology of temperature, which is much better than known aFGFs, including native human aFGF. As shown in the example of the invention, the peptide aFGF135 was in the status of a correct folding without denaturation or hydrolysis at body temperature (such as about 37° C.) for at least 48 hours of incubation (as shown in FIG. 1A). In another example of the invention, the peptide aFGF135 maintained its intact structure at a self accelerating decomposition temperature (such as about 54° C.) for an one-hour incubation (as shown in FIG. 1B). Accordingly, the peptide aFGF135 has a relatively high stability as compared with known aFGFs, such as known human aFGFs having 140 amino acids and 127 amino acids, respectively.

To show the distinctness between the peptide aFGF135 and the known aFGFs, NMR spectrograph was used to calculate the actual structure of the peptide aFGF135 in three-dimensions, and was compared with known aFGFs.

Figure 2:
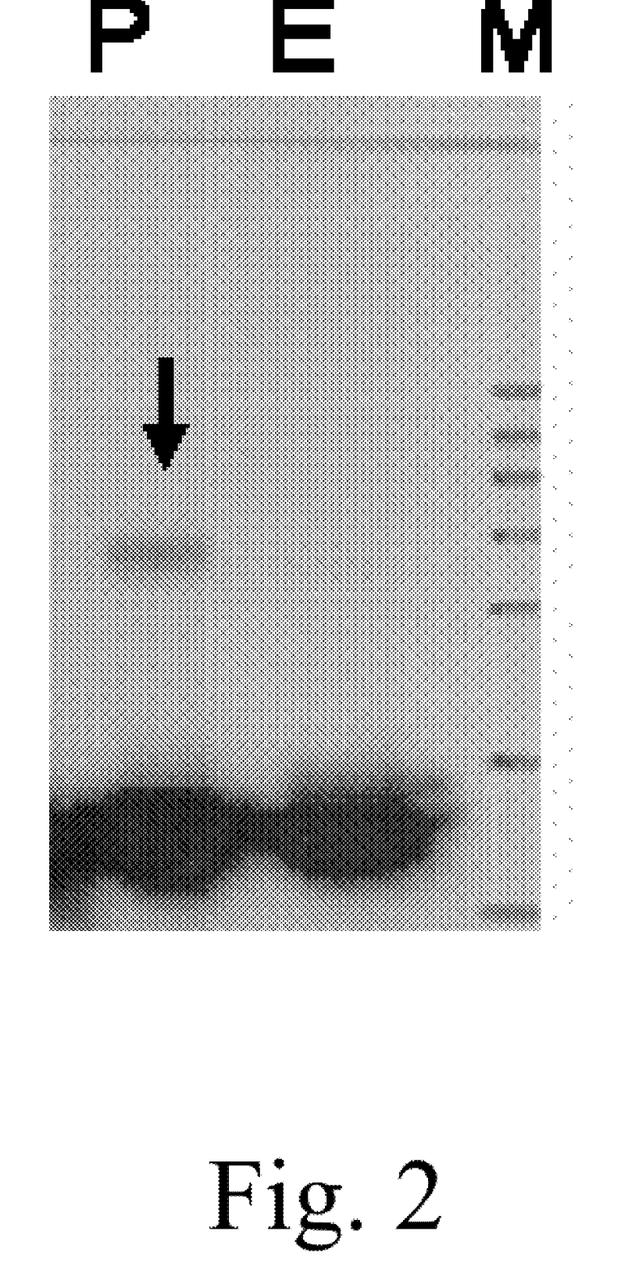
FIG. 2 is an image of the western blotting showing a comparison regarding the degradation between the peptide aFGF135 (shown as lane "E") and a commercial human aFGF having 140 amino acids (as lane "P") after an incubation at 54° C. for one hour; wherein lane "M" was the molecular markers and the degradation of the commercial human aFGF was presented in lane P, which was noted by a black arrow.
Figure 4A:
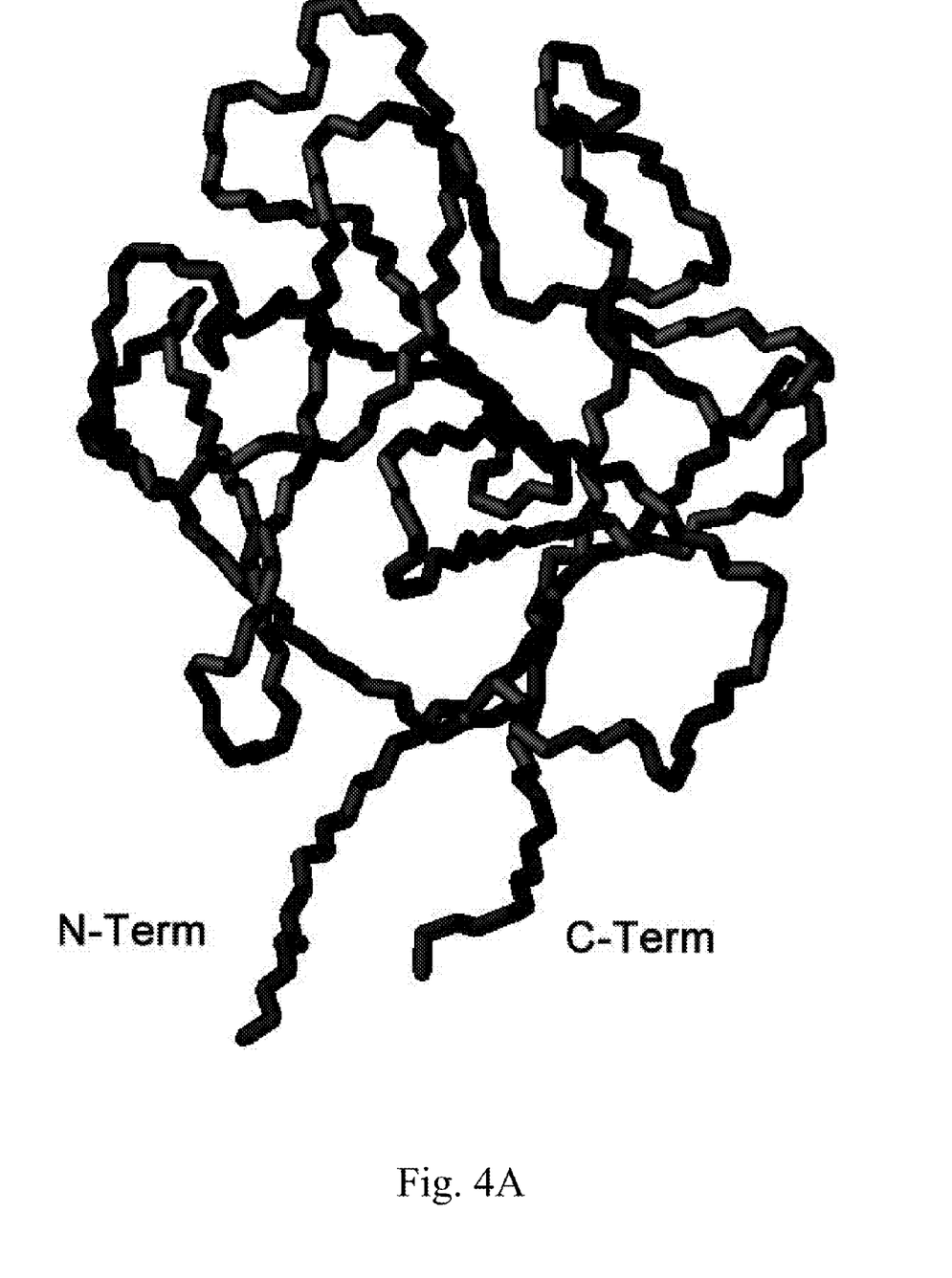
FIG. 4A is a 3D structure diagram of the peptide aFGF135 as predicted according to the $^1H^{15}N$-HSQC spectrum as shown in FIG. 3.

As compared with a human aFGF having 140 amino acids under Protein Data Bank (PDB) Code 1RG8 as published by Bernett M J et al. (*Proteins*, 57(3):626-34, 2004) and a human aFGF having 127 amino acids, PDB Code 1DZD as published by Lozano R M. Et al (*Biochemistry*, 2; 39(17):4982-93, 2000), the peptide aFGF135 has a different structural characterization, including C-terminal and N-terminal exposing and a distinct binding loop down left as shown in FIG. 4A. It suggests that the peptide aFGF with a modified sequence (including a deletion of 20 amino acids and an addition of Ala) causes a more stable structure than other known recombinant or natural aFGF. In one example of the invention, a comparison regarding stability in terms of degradation was conducted and the commercial recombinant aFGF (Promega Corporaton) showed a degradation band on the western blotting after a one-hour incubation at 54° C., but the peptide aFGF135 appeared stable, as shown in FIG. 2.

The present invention further provides a pharmaceutical composition comprising the peptide aFGF135 of the invention and a pharmaceutically acceptable carrier.

The pharmaceutical composition of the present invention can be manufactured by conventionally known methods with one or more pharmaceutically acceptable carriers. The term "pharmaceutically acceptable carrier" as used herein encompasses any of the standard pharmaceutical carriers. Such carriers may include, but are not limited to: saline, buffered saline, dextrose, water, glycerol, ethanol and combinations thereof.

The pharmaceutical composition of the present invention may be constituted into any form suitable for the mode of administration selected. Preferably, the composition is applied to the surgery area directly.

The present invention is further illustrated by the following examples, which are provided for the purpose of demonstration rather than limitation.

EXAMPLE 1

Cloning of the Peptide aFGF135

The full length of human aFGF was a product of Quick Clone cDNA bought from Clontech Laboratories, Inc. Before the construct, two specific primer sequences were designed as following:

SEQ ID NO: 2: 5'-ACTG▼AATTCATGGCTGAAGGGGAA ATCA-3'

SEQ ID NO: 3: 5'-AAGA▼AGCTTCATCAGA AGAGACTGGCAGG-3'

There was a EcoR1 restriction site in SEQ ID NO:2 (which is labeled as ▼), whereas a Hind III restriction site in SEQ ID NO:3 (which is labeled as ▼). The full length product was used to PCR amplification with the primers aforementioned, and a PCR product of 485 base pairs was obtained. After the recombinant cDNA reacted with restriction enzymes of EcoR1 and Hind III, the cut fragment was inserted into pUC18vector which had the same restriction sites.

According to the template of pUC-haFGF, two specific primer sequences were designed as following:

SEQ ID NO: 4: 5'-GGCA▼TATGGCTAATTACAAGAAGCCC-3'

SEQ ID NO: 5: 5'-AAGA▼GATCTCTTTAATCAGAAGAGACTGGCA GG-3'

There was a Nde I restriction site in SEQ ID NO:4 (which is labeled as ▼), whereas a Bgl II restriction site in SEQ ID NO:5 (which is labeled as ▼). The length of cDNA amplified by SEQ ID NO:4 and SEQ ID NO:5 was shortened by 57 base pairs from full length. The peptide aFGF135 had only 135 amino acids, and preserved the major functional domain of aFGF. Moreover, the secondary amino acid -Glycine (G) which was changed to Alanine (A) in N-terminal. It was shown as: ANYKKPKLLY in SEQ ID NO: 1. The cDNA fragment amplified by pUC18-haFGF was reacted with restriction enzymes of Nde I and Bgl II, and the cut fragment was inserted into pET3c vector which had the same restriction sites. As the result, a pET3c-haFGF was constructed.

EXAMPLE 2

Expression and Isolation of the Peptide aFGF135

After amplifying pET3c-haFGF, the vector was transformed to DNA with BL21(DE3) (Novagen, Germany) competent cell. The *E. coli* colonies resistant to ampicillin were cultured and amplified in LB medium to $OD_{600}$=0.3 before induction with final concentration of 1 mM IPTG (Isopropyl β-D-1-thiogalactopyranoside). After incubation for 16 hour (±2 hour), bacteria were collected and centrifuged with 27000×g to remove supernatant. The collected bacteria were washed with PBS twice, then lysed with a high pressure homogenizer (Niro Soavi model NS2006L, Daken Stainless Products Ltd., UK). The lysed sample was flowed trough a sieve with the pore size of 0.22 μm and ready for isolation of protein.

The peptide of human aFGF135 was isolated by the of chromatography as follows: (1) cation exchange chromatography (CMFF column, RM197, GE Healthcare Bio-Sciences USA Corp.); (2) affinity chromatography, which was specific to heparin (Heparin FF column, RM 244, GE Healthcare Bio-Sciences USA Corp.); and (3) size exclusion chromatography (Superdex 75 pre-grade column, RM245, GE Healthcare Bio-Sciences USA Corp.). The buffer used for the aforementioned columns was phosphate solution ($Na_2PO_4$: $NaHPO_3$=51:49 with 0.1% EDTA-Na, pH 6.8-7.2). The final product as obtained was the target peptide of the present invention. The molecule weight of the peptide aFGF135 was 15281 Da as determined by LC-MSMS assay.

EXAMPLE 3

Stability Test of the Peptide aFGF135

(I) Western Blotting Analysis

The crude peptides were subjected to SDS-PAGE in 4-20 or 10-20% gradient gels and then transferred to nitrocellulose membranes (0.05 μm; Schleicher & Schuell, Inc., Keene, N.H.) by electrophoresis' transfer (Polyblot Transfer System, Model SBD-1000; American Bionetics, Emeryville, Calif.). To investigate the stability of the aFGF peptides, Laemmli buffer (2.4 ml 1 M Tris pH 6.8, 0.8 g SDS-stock, 4 ml 100% glycerol, 0.01% bromophenol blue, 0.02% 1 ml β-mercaptoethanol (electrophoresis grade), and 2.8 ml water) with or without 8 M urea (to break up potential aggregates) was prepared as a stacking gel buffer including 0.0625 M Tris-base, SDS stock 1%, and dithiothreitol 15 mM. The samples were kept at room temperature for 1 h, then 4° C. overnight. It was boiled before loading onto SDS-PAGE.

After transferring and blocking of the nonspecific protein-binding sites with 3% dry milk in TBS, the nitrocellulose membrane was incubated with different antibodies at suitable dilutions (1:500 dilution of aFGF antibody, R & D Systems, Inc.) in wash buffer (10 mM Tris-HCl, pH 8.0, 0.15 M NaCl, 0.05% Tween-20) overnight at 4° C. Antigen-antibody complexes were visualized by incubating the membrane with suitable secondary antibodies and developing it by ProtoBlot Western Blot AP System (Promega, Madison, Wis.).

(II) Degradation Test

The intact aFGF peptides were incubated at 37° C. and 54° C., respectively, wherein 54° C. was a self accelerating decomposition temperature. Then, the samples were subjected to western blotting. The results for the samples after an incubation at 37° C. were shown in FIG. 1A, wherein lanes 1 to 3 were the results after 6 hours, 24 hours and 48 hours incubation, respectively, and lane 4 was the molecular marker, and the number above each of the bands represented the molecular weight. The results for the peptide aFGF135 after an incubation at 54° C. during a time period of 120 minutes (2 hours) were shown in FIG. 1B; wherein lanes 1 to 3 were the results after 10 minutes, 60 minutes and 120 minutes incubation, respectively, and lane 4 was the molecular marker, and the number above each of the bands represented the molecular weight.

As shown in FIG. 1A, the peptide aFGF135 maintained its intact structure at a body temperature (about 37° C.) for at least 48 hours. It indicated that the peptide aFGF135 provided a longer neural protection effect, and a better stability.

As shown in FIG. 1B, the peptide aFGF135 maintains its intact structure at 54° C. for at least 1 hour. When the peptide aFGF135 was incubated at 54° C. for 2 hour, it would fully degrade rather than transformed into other structure, which may cause an unpredictable risk of side effects. Subsequently, the peptide aFGF provided a safe storage or transportation.

Under the same experimental condition, the stability test was conducted for a commercial recombinant human aFGF having 140 amino acids ("Promega aFGF", from Promega Corporation). As shown in FIG. 2A, a second band as pointed out by a black arrow was presented in the band of Promega aFGF; on the contrary, the peptide aFGF135 maintained its structure without degradation. Meanwhile, when added the samples in a microplate, Promega aFGF appeared evidently white precipitate but the peptide aFGF135 appeared clear. It indicated that the peptide aFGF135 had a better stability than commercial aFGFs.

EXAMPLE 4

$^1$H—15N-NMR Structural Characterization

NMR spectroscopy is currently the popular techniques capable of determining the structures of biological macromolecules like proteins and nucleic acids at atomic resolution. The structural characterization for the peptide aFGF135 was conducted by High Field Nuclear Magnetic Resonance Center (Academia Sinica, Taiwan).

Figure 3:
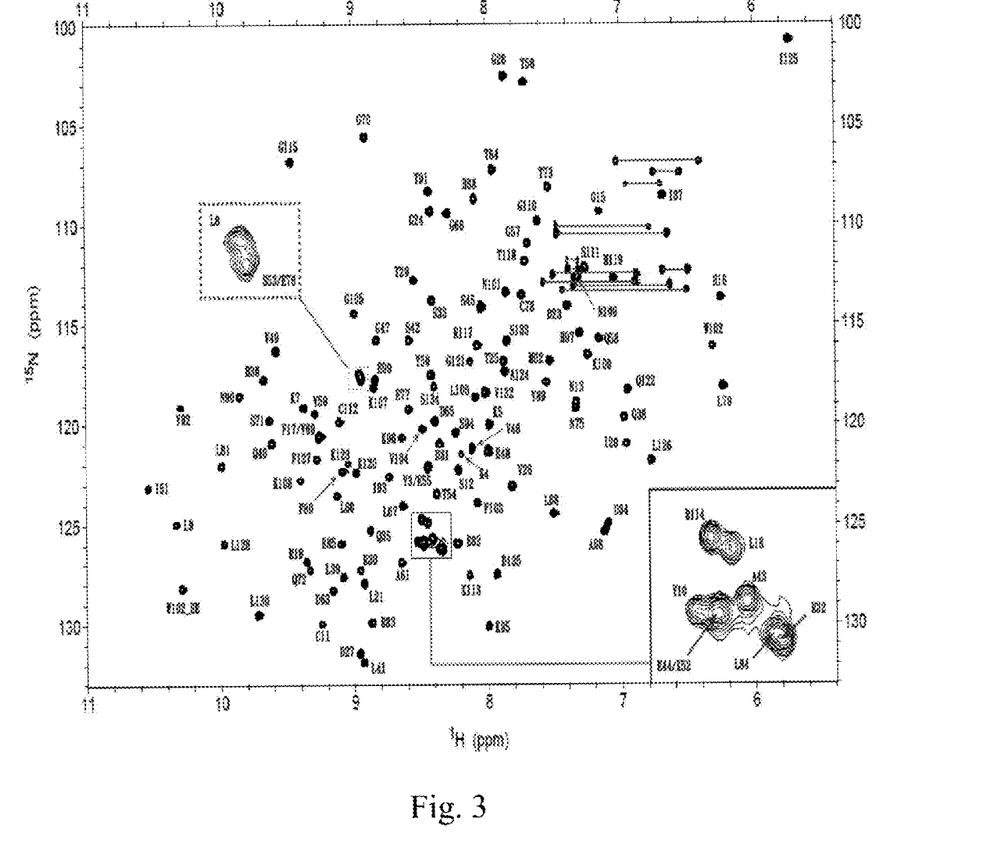
FIG. 3 is a diagram showing the $^1H$—$^{15}N$-HSQC spectrum of the peptide aFGF135 detected by a liquid-state protein NMR spectroscopy.

Briefly, the spectra were record at 298 K on Bruker AVANCE 600. C and N chemical shifts were used in the program TALOS to obtain backbone torsion angles. Sequence-specific resonance assignments for the backbone were accomplished using HNCO, HN(CA)CO, HACNCB, CBCA(CO)NH, HNCA and HN(CO)CA experiments, and side-chain assignments using $^{15}$N-TOCSY-HSQC and $^{13}$C-NOESY-HSQC in combination of $^{15}$N-NOESY-HSQC and $^{13}$C-NOESY-HSQC. The backbone spectrum was shown in FIG. 3.

For structure calculation, dihedral angle was obtained by program TALOS and distance limitation was obtained by $^{15}$N-NOESY-HSQC and $^{13}$C-NOESY-HSQC in combination of D2O exchange experiment to find 26 possible hydrogen bonds. The 3D structural characterization of the peptide aFGF135 was accomplished by the program CYANA as shown in FIG. 4A. NMR constraints and structure calculation statistics for Afgf135 were listed in Table 1.

TABLE 1

NMR Constraints and Structure Calculation Statistics for Afgf135[a]

| NOE distance constraints | |
| --- | --- |
| Total | 1639 |
| Short range, #i-j#ϕ1 | 869 |
| Medium range, 1 < #i-j# < 5 | 206 |
| Long range, 5 < #i-j# | 538 |
| Restrained hydrogen bonds | 26 |
| Torsion angle constraints | |
| Φ | 70 |
| Ψ | 76 |
| CYANA target function value (Å$^2$) | 1.26 ± 0.31 |
| Ramachandran plot statistics (%) | |
| Residues in most favored regions | 65.9 |
| Residues in additional allowed regions | 33.6 |
| Residues in generously allowed regions | 0.5 |
| Residues in disallowed regions | 0 |
| Root mean square deviation (RMSD) from the averaged coordinates (Å) | |
| Backbone RMSD of full length | 1.12 ± 0.36 |
| Heavy atom RMSD of full length | 1.56 ± 0.28 |
| Backbone RMSD of secondary structure[b] | 0.43 ± 0.08 |
| Heavy atom RMSD of secondary structure[b] | 0.93 ± 0.11 |
| Backbone RMSD of residues 7-12, 16-30, 36-53, 58-85, 89-108, 111-131[c] | 0.54 ± 0.07 |
| Heavy atom RMSD of residues 7-12, 16-30, 36-53, 58-85, 89-108, 111-131[c] | 1.05 ± 0.06 |

[a]The value given corresponds to the average over the 20 conformers that represent the solution structure from CYANA
[b]Secondary structure region is based on MOLMOL selection: 7-11, 16-21, 25-29, 39-43, 48-53, 59-62, 68-71, 80-85, 89-94, 127-131
[c]Selected region corresponding to region selected in Lozano RM. Et al (Biochemistry, 2; 39(17): 4982-93, 2000)

Figure 4B:
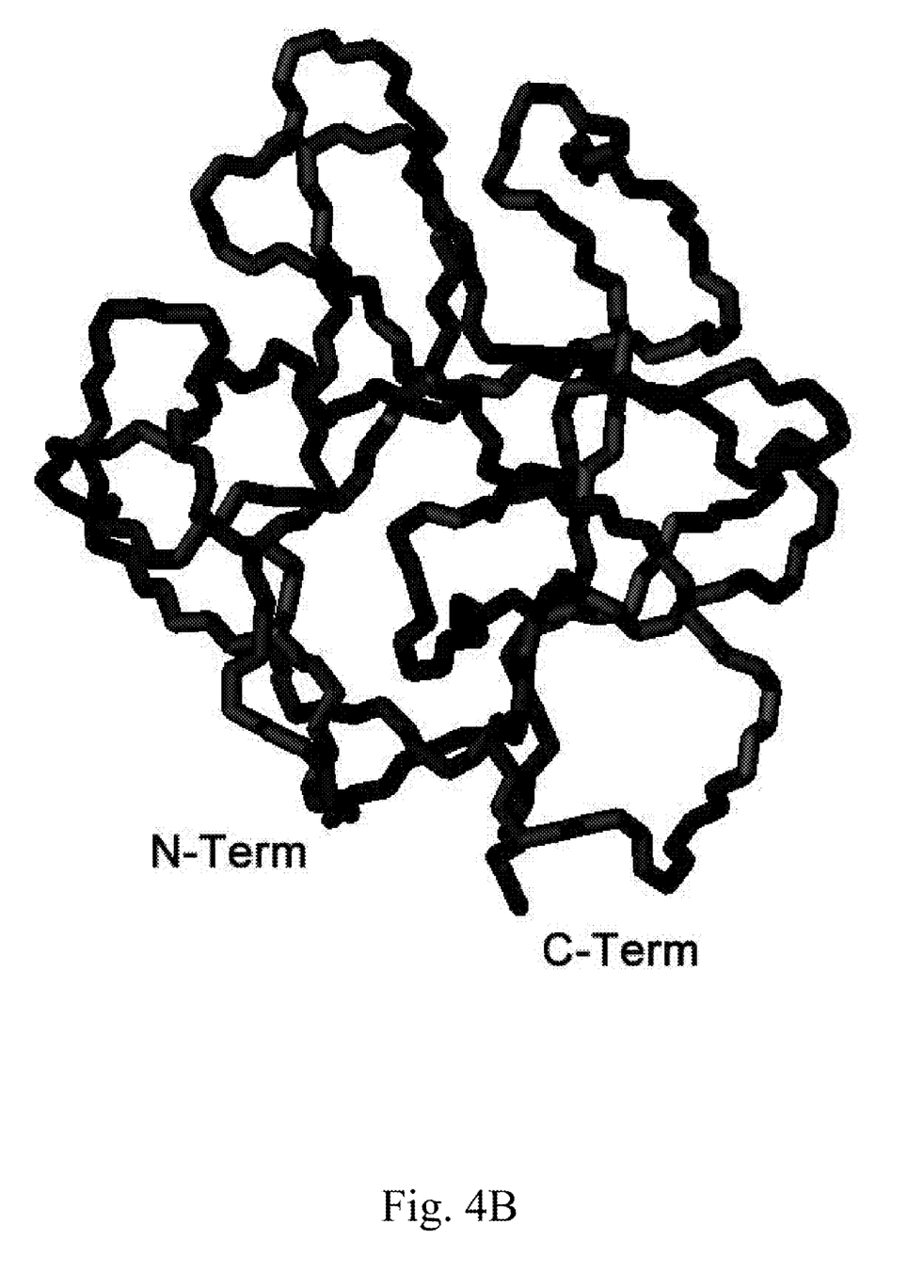
FIG. 4B is a 3D structure diagram of a human aFGF having 140 amino acids under PDB Code 1RG8.
Figure 4C:
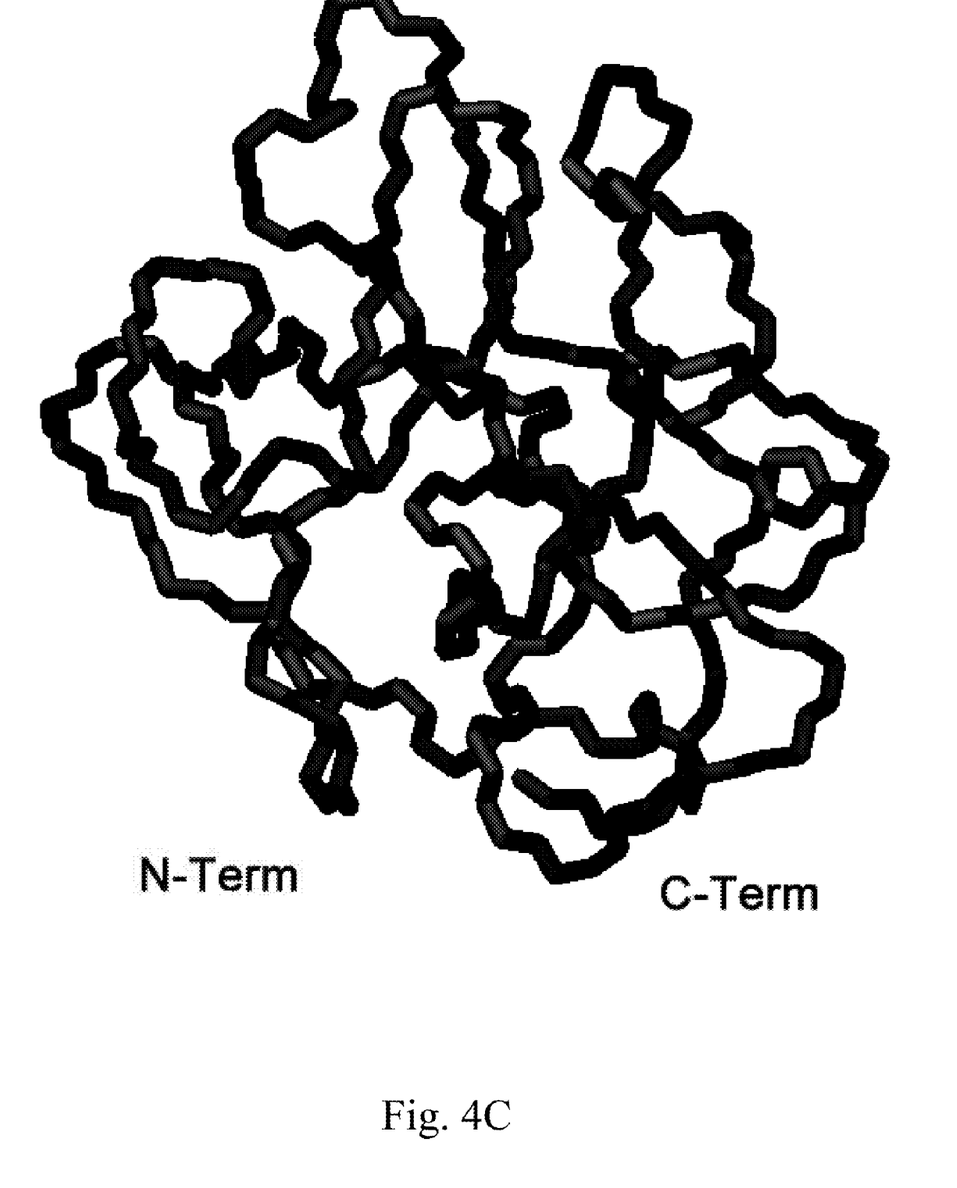
FIG. 4C is a 3D structure diagram of a human aFGF having 127 amino acids under PDB Code 1DZD.

The 3D structures of the peptide aFGF135 and two known human aFGF structures were shown in FIG. 4B and FIG. 4C for comparison. The aFGF having 140 amino acids of SEQ ID NO:6 under PDB Code 1RG8 had a structure shown in FIG. 4B; and the aFGF having 127 amino acids of SEQ ID NO:7 under 1DZD had a structure shown in FIG. 4C. The both are structurally different from the peptide aFGF135 as shown in FIG. 4A, wherein the N-terminal and C-terminal are buried inside and lacks a binding loop down left. It indicated that the peptide aFGF135 with a modified amino acid sequence and a distinct structure is structurally new and different from known aFGF peptides.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A modified peptide of human acidic fibroblast growth factor (aFGF) consisting of the amino acid sequence of SEQ ID NO:1.

2. A pharmaceutical composition comprising the modified peptide of claim 1 and a pharmaceutically acceptable carrier.

* * * * *